United States Patent [19]
Coats

[11] Patent Number: 5,356,811
[45] Date of Patent: Oct. 18, 1994

[54] METHOD OF PROCESSING STABILIZED ALOE VERA GEL OBTAINED FROM THE WHOLE ALOE VERA LEAF

[76] Inventor: Billy C. Coats, 4433 Crooked La., Dallas, Tex. 75229

[21] Appl. No.: 60,237

[22] Filed: May 10, 1993

Related U.S. Application Data

[63] Continuation-in-part of Ser. No. 872,942, Apr. 21, 1992, abandoned.

[51] Int. Cl.$^5$ .................. C07G 17/00; A01N 65/00
[52] U.S. Cl. ................................ 435/267; 435/262; 424/195.1
[58] Field of Search ..................... 435/262, 267; 424/195.1

[56] References Cited

U.S. PATENT DOCUMENTS

| | | | |
|---|---|---|---|
| 3,878,197 | 4/1975 | Maret | 260/236.5 |
| 3,879,537 | 4/1975 | Van Scott | 424/311 |
| 3,920,835 | 11/1975 | Van Scott | 424/311 |
| 3,984,566 | 10/1976 | Van Scott | 424/283 |
| 4,021,572 | 5/1977 | Van Scott | 424/317 |
| 4,105,783 | 8/1978 | Yu | 424/283 |
| 4,197,316 | 4/1980 | Yu | 424/317 |
| 4,234,599 | 11/1980 | Van Scott | 424/279 |
| 4,363,815 | 12/1982 | Yu | 424/274 |
| 4,380,549 | 4/1983 | Van Scott | 424/317 |
| 4,966,892 | 10/1990 | McAnalley | 514/54 |
| 4,996,062 | 2/1991 | Lehtonen | 426/8 |

OTHER PUBLICATIONS

Webb (Ed.), Enzyme Nomenclature, 1984, Academic Press, Inc., New York, pp. 51 and 109.

*Primary Examiner*—Irene Marx
*Assistant Examiner*—Maria Luisa Osoteo
*Attorney, Agent, or Firm*—Harris, Tucker & Hardin

[57] ABSTRACT

A process for preparing a stabilized aloe vera gel which includes separating the clear gel from the whole leaf of the aloe vera plant, by grinding and mixing the whole leaf with a cellulose dissolving compound. Clear aloe vera gel is obtained through a series of filtration steps. A selected quantity of an oxygen scavenging enzyme, such as glucose oxidase is added to the mixture to remove oxygen from within the gel and inhibit the growth of aerobic bacteria therein, and ultra-violet light is used to sterilize the gel without the addition of heat thereto. The material can be passed through a final organic filter to remove any remaining bacteria.

3 Claims, No Drawings

METHOD OF PROCESSING STABILIZED ALOE VERA GEL OBTAINED FROM THE WHOLE ALOE VERA LEAF

This is a continuation-in-part of copending application Ser. No. 07/872,942, filed Apr. 21, 1992, now abandoned.

BACKGROUND OF THE INVENTION

1. Field of the Invention

The invention relates to a method of preparing stabilized aloe vera gel, and, more particularly, to a cold process for preparing aloe vera gel from the whole leaf that allows for both topical applications and internal applications.

2. History of the Prior Art

Aloe vera is a subtropical plant which has elongate leaves containing a clear, viscous gel. The leaves are given structural rigidity by means of a plurality of hair-like connective fibers which run throughout the leaf. The plant is the source of at least two medicinal substances which includes a mucilaginous yellow fluid which comes from the base of the leaves of the plant adjacent the leaf rind. This yellow fluid is known as aloin and has been used throughout history as an active ingredient in cathartics and medicinal purges. The other medicinal substance which comes from aloe vera is the clear gel taken from within the body of the elongated leaves. This gel has been used throughout history for its therapeutic healing effect on burns, insect bites, and other human and animal injuries.

The therapeutic efficaciousness of the clear gel taken from aloe vera leaves is a function of the freshness of the gel. For example, exposure of the gel to light and air for about 1 ½ hours greatly diminishes the therapeutic power of the gel and may totally destroy it for some applications. For other applications, it has been found that relatively old, unstabilized gel has been effective. This difference is apparently a function of the fact that the gel itself is a complex mixture of components which are affected in varying degrees by exposure to air and light at different temperatures and which may vary from batch to batch of gel.

In addition to the decay of efficaciousness of the clear aloe vera gel upon exposure to light and air, the substance produces decomposition products which catalyze further decomposition over time. These phenomena render aloe vera gel extracts extremely difficult to compound into cream emulsions for topical applications. Cosmetic preparations of aloe vera usually become discolored after about four weeks and, further, the gel typically becomes rancid and totally unusable within the same time period.

One of the goals of prior art techniques of preparing stabilized aloe vera gel has been to preserve its medicinal efficacy as well as stabilize it for use in cosmetic preparations. The techniques taught in prior art U.S. Pat. No. 3,892,853 to Cobble and 4,148,372 to Coats have been relatively effective for many applications. However, both of these processes involve a step in which the temperature of the aloe vera gel and catalytic additives range from 35° C. to about 80° C. This addition of heat is necessary in order to destroy the aerobic bacteria within the gel and thereby sterilize it to inhibit decay. Most all of the organisms which cause decay in the therapeutic properties of the aloe vera gel are aerobic and, thus, without sterilization, the substance becomes rancid and essentially unusable within a relatively short period of time. The application of heat to the gel, however, also produces adverse side effects. Among these side effects are the fact that the heat destroys a substantial portion of the active ingredients within the gel and, thus, inhibits its efficacy as a medicinal compound. For example, heating of the gel contributes to the destruction of mucopolysaccharide as well as other enzymes and proteins which are believed to be responsible for a substantial portion of the therapeutic effects of aloe vera gel.

While processes for preparing aloe vera gel extract without the application of heat are known, see for example U.S. Pat. Nos. 4,735,935 and 4,851,224 to McAnalley, such cold processes have generally removed the outer skin of the aloe vera leaf before further processing. It is believed that the skin of the leaf, and the regions just below the skin, contain substantial quantities of highly active mucopolysaccharide compositions. Thus, fileting of the leaves to remove these regions results in a loss of efficacy of the final aloe vera product.

Other cold processes for preparing aloe vera gel extract are known which use the whole leaf of the aloe vera plant. However, these processes usually contain a chemical compound that is used for the purpose of killing bacteria. Due to the nature of these compounds, they have not been approved by the Federal Drug and Food Administration for internal consumption. This limits the gels and creams made from these processes to topical applications only.

Therefore, it can be seen that there is a need for a means for preparation of the purified aloe vera gel composition in both its untreated and hypoallergenic varieties without the application of heat that would allow retention of all of the valuable efficacious material contained within the region of the outer skin of the leaf. Furthermore, the provision of a cold process for preparing aloe vera gel from the whole leaf that could be taken internally would allow for greater diversification in the application of the final product.

SUMMARY OF THE INVENTION

The present invention is directed to a method of producing a stabilized aloe vera gel without the introduction of heat to the composition. More particularly, one aspect of the invention is directed to a process for producing an aloe vera gel product by slicing and grinding the entire aloe vera leaf, and mixing in a select quantity of a cellulose dissolving compound to the composition in sufficient quantities to separate the aloe vera from the ground leaf. The material is then pumped through a finisher apparatus which separates the leaf portion from the aloe vera gel. The aloe vera gel is then pumped into a tank where activated powdered carbon is added to absorb and remove the aloin form the aloe vera gel. In order to remove the powdered carbon containing the aloin, the gel mixture containing the powdered carbon is then passed through a press filter. These steps are accomplished without the addition of heat, and in a manner maximizing the efficaciousness of the gel product.

In another aspect, the invention includes adding a glucose oxidase and catalase in the correct compositions to the ground mixture described above. Such a step inhibits aerobic organisms from growing within the aloe vera gel and can thereby sterilize it without the addition of heat and the resultant problems associated with it. Other sterilization steps may include exposing the aloe vera mixture to ultraviolet light and passing the gel through one or more small micron filters before being passed into a storage receptacle. The aloe vera gel prepared by the present invention is more effectively produced and in a composition which is resistant to degradation upon contact with air and light. It also has a higher level of medicinal efficacy, retaining its medicinal characteristics to a much greater efficacious degree for an extended period of time. Additionally, the glucose oxidase has been approved by the Federal Food and Drug Administration for internal consumption which allows the products obtained from this process to be taken internally if necessary.

DETAILED DESCRIPTION OF THE PREFERRED EMBODIMENT

The raw material for preparing the cold process stabilized aloe vera gel is obtained from the leaves of fully mature aloe vera plants. Preferably, four to five year old plants are used to ensure full maturity to obtain a higher quality of leaves containing a larger amount of gel. Also preferably, the plants are grown under controlled conditions so that the size and structure of the leaves are more uniform, enabling accurate measurement and selection of quantities of materials to be used in the purification process.

Preferably, the aloe vera leaves are processed as soon as possible after cutting from the plant. This prevents as much degradative decomposition of the gel material as possible which begins upon cutting due to natural enzymatic reactions as well as growth of bacteria within the gel due to the presence of oxygen. After cutting, the aloe vera leaves are washed in water or a water and detergent mixture. The leaves are then washed with a suitable non-irritative bactericide and fungicide. For example, the leaves can be soaked in a water and chlorine solution for about 5 to 10 minutes. The leaves are then rinsed with sterilized water, and dried in a fashion not to obtain any lint on the leaves.

The aloe vera gel is separated from the leaf by first slicing and grinding the leaves. Any grinder known in the aloe vera art can be used. An example of an acceptable grinder is the Fritz Mill having a blade approximately 12 inches in diameter and a structure so as to perform a shearing action on the aloe vera leaves. The leaves are rotated in the container at approximately 750 RPM until thoroughly ground. The grinding can usually be accomplished in approximately one minute. However, depending on the RPMs, grinding can take a longer or shorter period of time. The ground leaf mixture is then homogenized in a mixer or blender.

A cellulose dissolving compounds known in the aloe vera process art may be added to facilitate the separation of the aloe vera gel from the leaf if so desired. The aloe vera gel is held in the leaf by a matrix of interstitial fibers, and though the grinding action may be sufficient to remove the gel form the leaf, a cellulose dissolving compound ensures complete separation. If so used, the cellulose dissolving compound is added in a quantity of approximately 20 grams per 55 gallons of the sliced and ground mixture. An example of the cellulose compound that can be used is CELLULASE 4000, manufactured by Miles Laboratories.

The liquid phase of the ground leaf mixture, which consists of clear aloe vera gel and aloin, must be separated from the solid phase, which consists primarily of the leaf pulp. It has been found that any finisher known in the aloe vera art can be used to accomplish this separation. However, an example of a finisher that can be used in accordance with this invention is the UCF-200A Finisher manufactured by FMC Corporation of San Jose, Calif. The ground leaf mixture is fed into the finishing cavity, which is a space created by a spiral with specially designed flights and contained inside are a plurality of 360° cylindrical screens having openings on the order of one-quarter of an inch in diameter, to remove the large green pulpy portions, and ending with one having an opening on the order of 0.5 microns in diameter. As the spiral rotates, the more liquid phase of the ground leaf mixture is separated from the solid phase as the liquid phase migrates toward the area outside the screen. Once through the screen, the liquid phase flows into a fully enclosed stainless steel pan. At this point, the aloe vera mixture is generally clear yellow color in appearance. The yellow color is due to the presence of the aloin in the aloe vera mixture. Once separated from the liquid phase, the solid phase of the ground leaf mixture is discarded.

Powdered activated carbon is added to the aloe vera mixture to absorb the unwanted aloin. The mount of activated carbon used, the time which the carbon is mixed with the aloe vera mixture and the temperature of the mixture may all vary. Preferably, however, approximately 2 lbs. of powdered activated carbon per 50 gallons of aloe vera mixture is added and mixed for approximately 12 hours at 70° Fahrenheit. The powered carbon can then be removed by a filtering process. Enough of the aloin-laded powdered carbon must be removed by filtering to produce a clear aloe vera mixture. A clear aloe vera mixture is a mixture that is substantially aloin free, i.e. the aloin content is less than 1 ppm.

The filter that removes the carbon from the aloe vera mixture is preferably a filter press. Use of the filter press is well known in the art of aloe vera manufacturing. A typical filter press is cylindrical in shape and the filter press and filters are arranged in a horizontal position. On both ends of the stainless steel filters are plates which can be mechanically manipulated against the filters so as hold the filters in place and can also be loosened to allow for removal of the filters. The filter press has an inlet opening to allow for the injection of the mixture to be filtered and an outlet end for extruding the filtered mixture. The mixture is forced through the filter press under pressure. An example of a filter press that can be used in this process is the STAR stainless steel filter press model 107 manufactured by Star Tank and Filter Corporation of Bronx, N.Y. This mixture is then recycled through the filter press several times, under pressure, until a clear aloe vera is obtained. A filter aid, such as diatomaceous earth, can be added to the aloe vera mixture to enhance the faltering ability of the filter press, if so desired.

An alternative filtering device can be used if so desired. In place of the filter press, the carbon can be faltered out of the aloe vera mixture by using a bag filter. A filter aid, such as diatomaceous earth, may be added to the aloe vera mixture. Again, the aloe vera mixture is forced through the bag filter under pressure. As the aloe vera mixture is repeatedly pumped through the bag filter, the filtering agent earth coats the bag and creates a very fine filtering system. Once the bag is sufficiently coated, the diatomaceous earth removes the carbon from the aloe vera mixture.

If so desired, the mixture can be passed through an additional filter system to insure removal of any remaining small amounts of carbon and other unwanted material, if so desired. An example of such a filter system is a series of organic cartridge filters that are capable of removing material from the aloe vera mixture down to a size of on the order of 10 microns. The organic filters used in this step of the process are generally the cartridge type of filters that are commonly used in the pharmaceutical industry. The cartridge filters can consist of a densely packed fiber material, or they can consist of either a polypropylene or a positively charged polypropylene material. For example, the type of filters that can be used are the Profile® II Filters manufactured by the Pall Corporation of East Hills, N.Y.

Bacteria removal is an important step in the present invention. Bacteria removal can be accomplished by using a combination of methods to assure that all bacteria are removed. This can include the use of chemical compounds such as glucose oxidase, ultraviolet light and the use of bacteria removing filters.

Sodium benzoate is added in sufficient quantities to obtain a 0.1% solution of sodium benzoate in the final mixture and a 0.1% solution of glucose oxidase/catalase is also added. The mixture is then homogenized by means of a mixer or blender and is mixed thoroughly for about 10 minutes. The gel is then allowed to sit for approximately 1 hour. Then, enough citric acid is added to the gel to adjust the pH to about 3.6.

Although glucose oxidase may be used alone as an oxygen scavenging enzyme, it has been found that a mixture of that enzyme with catalase is preferable. In particular, liquid solutions of glucose oxidase ($\beta$-D-glucose:oxygen 1-oxidoreductase) and catalase (hydrogen-peroxide:hydrogen-peroxide oxidoreductase) in a ratio of about 3.8 glucose oxidase unit/ml to about one catalase unit/ml. A unit of glucose oxidase, as described herein, is defined as that quantity of enzyme required to use 10 mm$^3$ oxygen per minute in a Warburg manometer at 30° C. in the presence of excess air and excess catalase with a substrate containing 3.3% glucose monohydrate and 0.1M phosphate buffer, pH 5.9 with 0.4% sodium dehydroacetate. A unit of catalase, as described herein, is defined as the mount of enzyme which degrades about 60 micromoles of hydrogen peroxide in one minute under assay conditions. The glucose oxidase/catalase preparation is used to scavenge oxygen from within the aloe vera gel material to remove as much oxygen as possible from within the substance. While the exact amount of glucose oxidase/catalase which is necessary to obtain the desired reaction may vary because of the varying chemical characteristics of the aloe vera gel matrix, normally, from about 5 to about 100 titrimetric GO units (glucose oxidase units) of glucose oxidase at about 24° C. temperature, per milliliter of finished aloe vera gel has been proven effective. Of course, other concentrations of glucose oxidase can be employed with the preferred amount of glucose oxidase being on the order of about 20 titrimetric GO units per milliliter of aloe vera gel. It should be noted that the maximum indicated quantity of the glucose oxidase preparation is several times that which may be minimally necessary to provide the scavenging of oxygen from the aloe vera gel matrix substance. The excess of glucose oxidase is used to accommodate the internal variation in the amount of gel substances which may occur from batch to batch and does not affect the scavenging of the oxygen of this step. In general, excess quantities do nothing more than dilute the gel preparation, but if they are added in extreme amounts, they may create certain difficulties. Excess amounts of the glucose oxidase also serve to act as a continual natural purification agent so that in the event that oxygen does enter the gel, it will be promptly scavenged by the glucose oxidase and not available for providing a medium for the growth of aerobic bacteria within the gel substance.

The aloe vera mixture is exposed to an ultraviolet light that has an approximate wavelength of 254 nm (nanometers) to kill any remaining bacteria. In one embodiment of the present process, the mixture is exposed to the ultraviolet light in a sterilizing chamber. Inside the sterilizing chamber, the ultraviolet light tubes are enclosed in a clear durable transparent material capable of heavy industrial use, such as glass or quartz. This protects the ultraviolet light and keeps the light from coming into contact with the mixture. Preferably, the tubes are made of quartz because quartz is capable of transmitting 95% of the ultraviolet light.

As the mixture flows through the chamber, it contacts a turbulence-creating device that causes the mixture to spin rapidly over and around the quartz sleeves. This maximizes the time microorganisms spend next to the ultraviolet light source and ensures they receive the required amount of ultraviolet light energy. The mixture is flowed into a tank and recycled back through the ultraviolet light chamber repeatedly for approximately 5-10 minutes, and more preferably for about 10 minutes.

If so desired, the mixture can then be passed through a final filter system that is capable of removing any last traces of bacteria. This assures removal of any remaining bacteria, mold or yeast. As before, these filters are also the cartridge type filters that are typically used in the pharmaceutical manufacturing industry. However, the filters used in this step of the process should be able to remove materials from the aloe vera mixture down to a size on the order of 0.2 microns. This removes anaerobic bacteria and thereby sterilizes the material.

Prepared gel treated as described above has been found to possess all the known healing qualities of fresh aloe vera gel in full potency for periods of at least 24 months. The resultant clear aloe vera mixture contains more mucopolysaccharide than that obtained from aloe vera preparations from which the skin of the leaf was removed before processing. In fact, the aloe vera mixture obtained by the present invention has been tested under the Swins Assay Standard to be 5.3 times stronger (530%) than aloe vera obtained by the hand fileted or machine extracted methods. The high percentage of aloe vera is attributed to the superior process of the present invention. Because the present process provides for the use of the whole leaf, the regions just below the skin that contain substantial quantities of the highly active mucopolysaccharide composition are retained in the aloe vera gel and are not discarded.

One additional step may be alternatively added to the process. This includes adding to the organically filtered whole leaf aloe vera material a small quantity of mucopolysaccharide powder separately extracted from aloe vera. For example, 10 grams of the material mucopolysaccharide powder made by Coats Aloe International Incorporated may be added to make an enhanced whole leaf aloe vera product.

EXAMPLE

The following example is set forth for the purpose of illustrating one embodiment of the present invention and is not to be interpreted as a limitation there of or in any limiting fashion.

Mature aloe vera leaves were cut from the plant. Approximately 1000 pounds of leaves were then washed in soapy water. The leaves were sliced and ground, an CELLULASE 4000 in proportions of 20 grams per 55 gallons of liquid was added. The gel was separated from the leaves with a pulper/finisher model PF 200 or MCF 200 by FMC Co. The ground leaf mixture was then passed through 360° cylindrical screens having openings on the order of one-quarter of an inch in diameter, to remove the large green pulpy portions, and ending with one having an opening on the order of 0.5 microns in diameter.

Approximately 2 lbs. of powdered activated carbon per 50 gallons of aloe vera mixture was then added to the aloe vera mixture. This mixture was then mixed for approximately 12 hours and was then pumped, under a pressure from about 20 psi to 80 psi at approximately 70° Fahrenheit and put through a filter press having a plurality of stainless steel filters 16 inches in diameter. The mixture was recycled through the filter press until a clear solution of aloe vera gel, substantially free from the aloin laded powdered carbon (i.e. where the aloin was 1 ppm) was produced. The mixture was then passed through a cartridge falter that removed any material from the aloe vera mixture down to a size of on the order of 10 microns.

The liquid was then flowed into a stainless steel tank where it was mixed with 12.8 ounces of sodium benzoate and approximately 1 liter of 0.1% solution of glucose oxidase/catalase ($\beta$-D-glucose:oxygen 1-oxidoreductase/hydrogen-peroxide:hydrogen-peroxide oxidoreductase) per 100 gallons of aloe vera gel mixture. This mixture was then mixed thoroughly for about 10 minutes. The gel was then allowed to sit for 60 minutes and citric acid was then added to the substance. Subsequently, enough citric acid was added to the solution to adjust the pH of the composition to about 3.6.

The aloe vera mixture was then passed under an ultraviolet light having an approximate wavelength of 254 nanometers at the rate of approximately 30 gallons per minute and then temporarily stored in a filling tank. The mixture was recycled under the ultraviolet light repeatedly for approximately 10 minutes. The mixture was then passed through a final filter system that removed materials, including bacteria from the aloe vera mixture down to a size of on the order of 0.2 microns. The filtered mixture was then transferred to a bottling machine.

After treatment in this manner the aloe vera composition may be concentrated by lyophilization with liquid nitrogen to a predetermined concentrate volume if desired. It may then be transferred to amber bottles and kept in a cool place for future use. Or, as an alternative, it may be stored without such concentration in plastic-lined barrels.

The stabilized aloe vera gel preparations of the subject invention can be effectively employed as a vehicle for antibiotics, steroids, local anesthetics, and many other preparations. In this capacity, the ability of the stabilized aloe vera gel to penetrate the skin surface and carry other medication with it is especially useful. In its preferred form, it was found that the aloe vera gel preparation of the subject invention had enhanced efficacy as well as enhanced ability to remain stable and unrancid for substantial periods of time.

While the invention has been described in relation to its preferred embodiments, it is to be clearly understood that various modifications of the invention will now be apparent to ones skilled in the art upon reading the subject specification and it is intended to cover all such modifications that fall within the scope of the appended claims. For example, the glucose-oxide mixture may be added prior to the removal of the aloin with the powdered activated carbon or the U.V. sterilization may be performed before or the optional final filtering process.

What is claimed is:

1. A process for extracting aloe vera gel from the leaf of aloe vera without the application of heat, the process comprising the steps of:
    (a) mechanically slicing and grinding whole aloe vera leaves;
    (b) mixing the ground aloe vera leaves in the presence of approximately 20 grams per 55 gallons of a cellulose dissolving compound comprising cellulase to form a mixture of aloe vera gel, aloin and aloe vera leaf pulp;
    (c) removing the aloe vera leaf pulp by extruding the mixture through at least one filter to obtain an aloe vera gel and aloin mixture;
    (d) adding approximately two pounds of activated powdered carbon per 50 gallons of aloe vera gel and aloin mixture obtained in step (c) to absorb the aloin;
    (e) removing the aloin laded activated powdered carbon to obtain aloe vera gel having an aloin content of less than about 1 ppm;
    (f) extruding the aloe vera gel obtained in step (e) through at least one filter that removes carbon material from the mixture down to a size on the order of 10 microns;
    (g) mixing the aloe vera gel obtained in step (f) with a solution of glucose oxidase and catalase in a ratio of about 3.8 glucose oxidase units to about 1 catalase unit and with approximately 12.8 ounces of sodium benzoate per 100 gallons of the mixture;
    (h) exposing the aloe vera gel obtained in step (g) to ultraviolet light radiation having an approximate wavelength of 254 nanometers for approximately 10 minutes; and
    (i) extruding the aloe vera gel obtained in step (h) through at least one organic filter.

2. The process of claim 1 wherein the glucose oxidase of step (g) is added to the aloe vera gel in an mount from about 5 glucose oxidase units to about 100 glucose oxidase units per milliliters of aloe vera gel obtained in step (f).

3. The process of claim 1 wherein the at least one organic filter of step (i) comprises an organic filter having openings on the order of 0.2 microns.

* * * * *